United States Patent [19]
Yoon et al.

[11] Patent Number: 5,994,560
[45] Date of Patent: Nov. 30, 1999

[54] RESOLUTION OF RACEMIC MIXTURES USING POLYMERS CONTAINING CHIRAL UNITS

[75] Inventors: Hyun Nam Yoon; Mengshi Lu, both of New Providence, N.J.; Naoya Ogata, Tokyo, Japan

[73] Assignee: Hoechst Celanese Corp., Somerville, N.J.

[21] Appl. No.: 08/697,751

[22] Filed: Aug. 29, 1996

[51] Int. Cl.⁶ .................. C07D 209/20; C07B 57/00; C07C 51/43; C07C 53/134

[52] U.S. Cl. .................. 548/498; 548/495; 562/401; 562/402; 562/494; 562/496; 562/573

[58] Field of Search .................. 548/498, 495; 562/496, 573, 401, 402

[56] References Cited

U.S. PATENT DOCUMENTS 5,292,924  3/1994  Grosser et al. ..................... 560/41

OTHER PUBLICATIONS

Chemical Abstracts, vol. 118:39405, 1993.

Chemical Abstracts, vol. 125:87148, 1996.

Chemical Abstracts, vol. 112:111197, 1990.

*Primary Examiner*—Joseph McKane
*Assistant Examiner*—Dominic Keating
*Attorney, Agent, or Firm*—P. S. Kalyanaraman

[57] ABSTRACT

Described herein is a novel process to resolve a racemic compound into its optically active isomers without need for chemical transformation such as salt formation. The process advantageously utilizes polymers containing chiral moieties in their repeat units as well as exhibiting critical solution temperature behavior in a suitable solvent. An embodiment describes the resolution of tryptophan.

23 Claims, No Drawings

RESOLUTION OF RACEMIC MIXTURES USING POLYMERS CONTAINING CHIRAL UNITS

FIELD OF THE INVENTION

The present invention is generally directed to methods of separating racemic mixtures into D and L compounds and is specifically directed in its preferred embodiments to achieving that purpose by utilizing polymers containing chiral -either an R or S type- monomeric units and exhibiting critical transition temperature behavior.

BACKGROUND OF THE INVENTION

Resolution of racemic compounds is becoming an increasingly important industrial function for the last several years. This is because the resolved compounds, the optically active D or L isomers, have valuable utility and applications in fields such as, for example, drugs, fragrances, electronics and the like. Particularly in the pharmaceutical field, there is a great interest in optically active isomeric forms of drugs. See, for example, Chiral Drugs, S. C. Stinson, Chemical & Engineering News, American Chemical Society, Washington, DC, 44 (Oct. 9, 1995); idem, ibid., 38 (Sep. 27, 1993); and Chiral Drugs fast entering the Mainstream, Chemical Marketing Reporter, 5 (Jun. 10, 1996).

Obtaining optically active (chiral) isomeric forms of compounds has been traditionally achieved by processes such as, for example, chiral synthesis, asymmetric hydrogenation of appropriate precursors, enzymatic resolution, chromatic processes, and the like. However, such traditionally available synthetic methods to resolve racemates generally involve complicated or selective chemical reactions which necessitate a subsequent reverse reaction to yield the desired enantiomer; many of them are expensive and the yields are not always satisfactory. The enzymatic processes are generally slow. Since most chemical reactions result in the formation of racemates, an economical approach to resolving such readily available racemates would be the cheapest and easiest way to obtain chiral isomers.

Among chiral compounds, chiral amino acids are important commercial materials. Many resolution methods, particularly for amino acids, involve salt formation using resolving agents and reconversion. Many of these resolving agents are generally expensive. Among non-salt forming methods, ligand exchange chromatography has been proposed. Even here prior derivatization of the amino acid is sometimes necessary. See, for example, Kirk-Othmer Encyclopedia of Chemical Technology, John Wiley & Sons, Inc., New York, vol. 2, 521 (1992). Thus, there is a growing interest in finding inexpensive ways to resolve racemic mixtures into optically active isomers.

It is, therefore, an object of this invention to provide a viable process to resolve racemates into optically isomers.

It is another object of this invention to provide a process to separate racemates into optically active isomers without the need for salt formation.

It is yet another object of this invention to provide a process to separate racemic amino acids into optically active isomers.

Other objects and advantages of the present invention will be apparent from the accompanying summary, description and examples.

SUMMARY OF THE INVENTION

One or more of the foregoing objects are achieved by provision of the present process for resolving racemic compounds. The process is especially useful for resolving racemic amino acids into D and L compounds. The invention utilizes, as resolving agents, polymers which are temperature responsive and also contain optical active centers. This means that the polymers contain either R or S monomeric moieties and also exhibit critical solution temperature ("CST") behavior in a suitable solvent. The polymers may be homopolymers or copolymers containing such moieties. CST is a phase transformation property. For a discussion of the CST behavior of polymers, see, for example, L. Liebler, *Concise Encyclopedia of Polymer Science and Engineering*, J. I. Kroschwitz, ed., John Wiley & Sons, New York, p. 715–716 (1990). The CST may be Lower Critical Solution Temperature ("LCST") or Upper Critical Solution Temperature ("UCST"). Suitable solvents useful in the practice of the invention are, for example, water, alcohol, amides, ethers and the like as well as suitable combinations thereof.

In one illustrative embodiment, the polymer, containing either an R or S monomeric moiety as a covalently linked part of the polymer, and exhibiting LCST in water, is placed in solution in water, following which the racemic mixture of the compound to be resolved is added. The temperature is then raised above the LCST related to one enantiomer whereupon the polymer precipitates. Surprisingly, only one optically active isomer is preferentially adsorbed on the polymer. The precipitate is then separated from the solution, dissolved in water and the adsorbed enantiomer is separated from the polymer by any suitable process such as, for example, partitioning between water and a solvent.

An illustrative temperature responsive polymer is a copolymer of N-isopropylacrylamide ("IPPAAm") and S(+) or R(–) sec-butylacrylamide ("SBAAm"). This polymer, with up to 70 mole percent of SBAAm is water soluble and its solution exhibits LCST behavior. Thus, it is soluble in water below the LCST but precipitates when the temperature is raised above this temperature. When such a copolymer is dissolved in water and another chiral compound is added, the polymer's LCST behavior changes. Thus, for example, a copolymer of IPPAAm and R(+)-SBAAm (70:30 mole ratio) exhibits a slightly higher LCST in an aqueous D-tryptophan solution than in L-tryptophan solution (37° C. versus 32° C.). Because of this differential behavior, if the temperature is controlled between the two LCST temperatures, the polymer will precipitate and preferentially adsorbs one enantiomeric tryptophan from a solution of racemic tryptophan. Thus, the copolymer containing R-type SBAAM tends to strongly adsorb D-Try while the copolymer containing the S-type units tends to strongly adsorb L-Try. The selectivity is high enough to result in substantial enrichment of one isomer in the polymer leaving the other in the solution. The polymer containing the D- or L-Try becomes insoluble in water and precipitates which may then be filtered.

DESCRIPTION OF THE INVENTION

The inventive process employs a temperature responsive polymer that contains optically active (chiral) centers. The term 'temperature responsive' refers to the exhibition of critical solution temperature behavior by the polymer which property has been defined above. This means that the conformation of the polymer changes, e.g. from coil to globule, and the solution becomes two-phase, e.g. turbid, as the temperature is changed to above (or below) a certain value. Many polymers are known to exhibit CST behavior such as, for example, polyisoprpopylacrylamide, poly N-sec-butylacrylamide, polyalkenes and the like. The CST and phase transition behavior of poly(N- isoprpopylacrylamide) has been described, for example, by M. Heskins et al, *J. Macromol. Sci., Chem. Ed.,* Vol. A2, 1441–1455 (1968) and by M. Irie, *Advances in Polymer Science,* Vol. 110, 49–65 (1993). The CST may be LCST or UCST. For the practice of the present invention, the polymer must not only exhibit CST but must also contain chiral moieties. These chiral centers discriminate other enantiomeric isomers by shifting the CST. When mixed with a mixture of D and L compounds, the chiral polymer precipitates from the solution when the temperature reaches the CST related to one of the enantiomers and selectively adsorbs one of them, thus offering a novel method of separation.

The chiral centers may be part of a homopolymer or introduced into a polymer structure by way of copolymerizing a nonchiral monomer with a chiral monomer. Suitable chiral monomers include, for example, SBAAm, R or S-methyl benzyl acrylamide, or any other suitable acrylamide derived from the reaction between acryloyl chloride and a suitable R or S-primary or secondary amine, and the like, and combinations thereof.

The following description utilizes a copolymer of IPPAAm and SBAAm to separate tryptophan, and is for illustrating the present invention. Such a copolymer containing from 1 to about 70 weight % of SBAAm is water soluble, enabling practice of this invention in aqueous solution. Each such copolymer has its unique LCST in water and exhibits different LCST in the solution that contains optical enantiomers such as D- or L-tryptophan.

The invention begins with the synthesis of the optically active comonomer, S- or R-sec-butylacrylamide by reacting S-(+) or R-(−)-N-sec-butylamine with acryloyl chloride. Both materials are commercially available. Solvents such as, for example, hydrocarbons, ether, esters, ketones, halogenated hydrocarbons, amides and the like may be employed for the reaction. Acid-scavenging materials such as triethylamine, pyridine and the like may be employed as catalysts or cosolvents. The reaction is generally performed at low temperatures and under anhydrous conditions, as is known to those skilled in the art. In one typical preparation, the chiral amine and the acid chloride were reacted in methylene chloride at about 0–15° C. to yield chiral N-sec-butylacrylamide. This was purified and then copolymerized with N-isopropylacrylamide by conventional free radical polymerization using αα'-azobisisobutyronitrile ("AIBN") as the initiator in N,N-dimethylformamide ("DMF") at about 70° C. The copolymer composition was controlled through monomer ratio and was ascertained by $^1$H-NMR. The molecular weight of the copolymer was measured by GPC using DMF as the solvent.

The resolution process starts with dissolving the above-described chiral copolymer, in water below its LCST. A mixture of D- and L- (or racemic) tryptophan is added and the temperature is raised slowly. The copolymer containing R-(+) N-sec-butylacrylamide has a slightly higher LCST in D-tryptophan solution than in L-tryptophan solution (37° C. versus 32° C.). The copolymer containing only one type N-sec-butylacrylamide (R or S) selectively adsorbs one enantiomeric tryptophan in a racemic solution. By raising the temperature to between the LCST exhibited in D- and L-tryptophan solution, the copolymer containing R-type units strongly adsorbs D-Try while the copolymer containing S-type units strongly adsorbs L-Try. The other isomer substantially remains in the solution. The polymer with the adsorbed enantiomer starts to precipitate. The precipitate is separated by centrifuge. The unadsorbed isomer is recovered from the filtrate by removing the water suitably such as, for example, drying in vacuo or freeze drying. The adsorbed isomer may be recovered from the polymer precipitate by a suitable process such as, for example, partitioning between water and an organic solvent and extracting it out or by washing the polymer with hot water (the polymer remains as a gel-like solid while the adsorbed isomer is washed out). By repeating this process, if necessary, it is possible to separate the two enantiomers.

For comparison purposes, racemic N-sec-butylacryalamide was copolymerized with N-isopropylacrylamide. The polymers exhibited LCST behavior in water. While addition of racemic tryptophan solution changed the LCST, no differentiation was observed between D-Try and L-Try, making separation impossible. This clearly demonstrated the uniqueness and surprising aspects of the present invention to separate chiral isomers by making use the LCST behavior of chiral polymers.

In a similar manner, resolution of racemic phenylalanine by employing a chiral copolymer in a buffered aqueous solution could also be demonstrated, showing the wide applicability of the present invention to resolve racemic compounds.

The advantages of the instant process will be obvious to those skilled in the art. Some of them include, for example, an economical and fairly fast method of achieving the resolution without resorting to a chemical conversion such as, for example, diastereomer salt formation. Another advantage is the feasibility for scaling up to large scales of separation. Since many such separated isomers are highly valuable commercially, the instant process offers a unique way of preparing them by an economical route.

The following examples are provided for purposes of illustration only and not by way of limitation.

EXAMPLES

In the following Examples, g refers to grams, ml to milliliters, mmole to millimoles, and "ambient temperature" to temperatures in the range 22–28° C.

Example 1

Synthesis of R and S-sec-butyl acrylamide

R- and S-sec-butyl acrylamide were prepared by treating a solution of acryloyl chloride in methylene chloride at 0° C. with either R- and S-sec-butylamine. In a typical example, 9 ml of acryloyl chloride is added into a three-neck round bottom flask with 50 ml of methylene chloride. After purging with nitrogen, 8 grams of R or S-sec-butylacrylamide (one equivalent mole) plus 15.2 ml of triethylamine (one equivalent mole) are added dropwise to keep the reactor temperature below 5° C. After 4 hours of reaction, the methylene chloride solution was washed with aqueous acid, aqueous base, and water, and then dried and solvent was removed to yield the product. Yields were almost quantitative provided that the temperature did not rise above 10° C. during the reaction. $^1$H-NMR of final product confirmed its structure.

In a similar manner, racemic N-sec-butylacrylamide was also prepared from racemic sec-butylamine and acryloyl chloride.

Example 2

Synthesis of poly (N-isopropylacrylamide-co-N-R or S-sec-butylacrylamide)

N-isopropylacrylamide (commercial material) was purified by recrystallization from toluene/hexane (1/10, v/v).

N-R- or S-sec-butylacrylamide from Example 1 was used as it was. There are two ways to synthesize poly (N-isopropylacrylamide-co-N—R or S-sec-butylacrylamide), i.e., in an organic solvent and in water.

Polymerization in organic solvent 6 grams of a mixture of N-isopropylacrylamide and N-R- or S-sec-butylacrylamide in various ratios (see Table 1) were dissolved in 50 ml of DMF. The solution was degassed by bubbling with $N_2$ for 10 min. Then the solution was heated to 70° C. and 3 mg of AIBN was added. The polymerization was carried out for up to 24 hours. The polymer was recovered by precipitation in either (500 ml). The precipitate was filtered, washed repeatedly with diethyl ether, and dried in vacuo at 40° C. for 24 hours. Table 1 summarizes the characteristics of the synthesized copolymers.

In a similar manner, copolymers of N-isopropylacrylamide and racemic sec-butylacryalamide were also prepared.

TABLE 1

Properties of poly(N-isopropylacrylamide-co-N-R or S-sec-butylacrylamide)

| N-sec-butylacrylamide | Yield (%) | butylacrylamide:N-isopropylacrylamide[a] (mole) | $\overline{M}_w$[b] | $[\alpha]_D^{20}$ |
|---|---|---|---|---|
| 30 mole % | | | | |
| S-type | 34.1 | 30:70 | 6000 | +1.19 |
| R-type | 21.4 | 26:74 | 33000 | −0.90 |
| Racemic type | 36.6 | 26:74 | 7600 | 0 |
| 50 mole % | | | | |
| S-type | 37.1 | 50:50 | 8000 | +5.98 |
| R-type | 35.5 | 48:52 | 8600 | −7.47 |
| Racemic type | 40.6 | 50:50 | 7800 | 0 |
| 70 mole % | | | | |
| S-type | 32.8 | 64:36 | 11000 | +10.49 |
| R-type | 21.8 | 70:30 | 12000 | −14.93 |
| Racemic type | 29.8 | 68:32 | 12000 | 0 |

[a]determined by 1H-NMR.
[b]determined by GPC in DMF.
[c]measured by polarimeter at 20° C. (c = 1.18 × 10$^{-5}$ mol/1000 ml in water).

Polymerization in water 10 grams of a mixture of N-isopropylacrylamide and R or S-sec-butylacrylamide at various ratios are dissolved in 100 ml of deionized water. A solution of 100 mg of ammonium peroxydisulfate, $(NH_4)_2S_2O_8$, in 3 ml of deionized water is added slowly to the reactor as initiator. 200 mg of potassium metabisulfite, $K_2S_2O_5$, dissolved in 3 ml water, is added as accelerator. The solution is stirred at ambient temperature for 20 hours. The solution is then heated to 50° C. and filtered hot. The precipitate is then dissolved in 75 ml of tetrahydrofuran (THF) and reprecipitated using 400 ml of diethyl ether. Finally the polymer is redissolved in water and dried in vacuo.

Example 3

LCST Behavior of Racemic Copolymers; absence of selectivity between the tryltophan isomers The LCST behavior of racemic copolymers was characterized by measuring the optical transmittance of their 0.1 wt % aqueous solution in the absence or presence of D- or L-tryptophan as a function of temperature. The copolymer containing 30 mole % N-(+)-sec-butylacrylamide exhibited a LCST of 27° C., while the copolymer containing 50 mole % N-(+)-sec-butylacrylamide had a LCST of 22° C. The phase transition became broad with increasing content of the butylacrylamide. When D- or L-Try was added to the solution, however, the LCST shifted to a higher temperature (from 27° C. to 30° C.). This shift became larger as the content of the butylacrylamide was increased. (For 50:50 copolymer, the LCST shifted from 22 to 28° C.). However, since the copolymer used here was racemic, no differences in LCST was observed between D-Try and L-Try solution.

Example 4

LCST Behavior of Chiral Copolymers; selectivity between the tryptophan enantiomers In the absence of Try, the copolymer that contained either 30 mole % of R- or S-N-sec-butylacrylamide unit showed the same LCST (28° C.) in aqueous solution. However, when tryptophan was present, the LCST behavior was surprisingly different. The copolymer having 30% R-type units exhibited a higher LCST in D-Try solution (concentration: 0.226 mmole/liter) (34° C.) than in same concentration L-Try solution (30° C.). Likewise, the copolymer having 30% S-type units exhibited a higher LCST in the D-Try solution (38° C.) than in the L-Try solution (33° C.). Increasing the concentration of Try shifted the LCST to even higher temperature. Similar phenomena were observed for the copolymers containing 50 mole % of N—R- or S-sec-butylacrylamide units. This phenomenon was utilized to resolve racemic tryptophan as described below:

Optical resolution of DL-Tryptophan

Three copolymers that contained 50 mole % N-R-sec-butylacrylamide, N-S-sec-butylacrylamide and racemic N-sec-butylacrylamide were dissolved separately in water at 0.1 wt % concentration. Racemic tryptophan was subsequently added to each solution at 0.226 mmole/l concentration at 20° C. After the added racemic Try completely dissolved, the temperature of each solution was raised gradually from 20° C. to 30° C. at which point the solution became turbid. The precipitate that formed was separated by a centrifuge. The amount of Try remained in the aqueous solution was determined by high pressure liquid chromatography ("HPLC") and the adsorbed amount of Try was calculated. The copolymers containing chiral moieties showed resolution of the DL-tryptophan into the enantiomers while the copolymer containing no chiral moieties did not resolve it. Table 2 summarizes the results of these experiments.

TABLE 2

Selective adsorption of D- or L-tryptophan to 50:50 poly(N-isopropylacrylamide-co-N-sec-butylacrylamide)

| | Adsorbed amount of tryptophan* (mmole/l) | |
|---|---|---|
| Type of Copolymer | D-Try | L-Try |
| S-type | 0.012 (5.3%) | 0 |
| R-type | 0 | 0.015 (5.5%) |
| Racemic | 0.021 (9.2%) | 0.031 (13.2%) |

*initial tryptophan concentration was 0.226 mmole/l.

Example 5

Separation of the polymer and the adsorbed enantiomer

In one approach, the precipitate obtained by centrifugation in Example 4 is washed with hot water repeatedly. The adsorbed isomer dissolves in the water while the polymer remains as the solid phase. The two are separated by filtration, and the amino acid is recovered from the water solution suitably.

Example 6

LCST Behavior of Chiral Copolymers; selectivity between the phenylalanine enantiomers In this example, the LCST behavior was studied in a buffer solution. The buffer solution was prepared by dissolving 0.0623 g $KH_2PO_4$, 0.1224 g $Na_2HPO_4.12H_2O$ and 1.0 g $CaCO_3$ in 520 ml deionized water. The pH of the buffer solution was 7.4. The copolymer that contains 50 mole % N-S-sec-butylacrylamide units were dissolved in this solution at 0.1 wt % concentration at 10° C. The LCST of this solution was determined by monitoring the light transmittance while raising the temperature slowly. In the absence of phenylalanine, the LCST was found to be 14° C. When D-phenylalanine was added at 0.0625 mmole/l concentration to this solution, the LCST remained unchanged. On the other hand, when the L-isomer was added at the same concentration, the LCST shifted to about 17° C. This difference in the LCST of this copolymer between D and L-phenylalanine could be used to resolve racemic phenylalanine.

Optical resolution of DL-phenylalanine

A copolymer containing 50 mole % N-S-sec-butylacrylamide units was dissolved in a $KH_2PO_4$/$Na_2HPO_4$/$CaCO_3$ buffer solution (pH 7.4) at 0.1 wt % concentration at 10° C. Racemic phenylalanine was added to this solution at a 0.0625 mmole/l concentration. After the phenylalanine completely dissolved, the temperature of the solution was raised gradually from 10° C. to 17° C. and the solution started to turn turbid. The precipitate could be isolated through centrifugation and it was found to have adsorbed D-phenylalanine from the solution exclusively. The centrifugate contained all the L-isomer plus some unadsorbed D-phenylalanine. The amount of both isomers could be measured by HPLC., and the amount of adsorbed D-phenylalanine could be calculated.

What is claimed is:

1. A process of resolving a racemic amino acid into its optically active isomers, comprising:
   (a) preparing a solution of a chiral polymer in a suitable solvent, wherein said solvent is selected from the group consisting of water, alcohol, ether, amide, ester, ketone, and combinations thereof, further wherein said polymer is either a homopolymer of a chiral monomer, or a copolymer of N-isopropylacrylamide and a chiral comonomer, with said polymer exhibiting critical solution temperature behavior in said solvent;
   (b) maintaining said solution at a temperature different from said critical solution temperature such that the polymer stays in solution;
   (c) mixing the racemic amino acid intimately with said solution such that said chiral moieties shift said critical solution temperature differentially corresponding to the optically active isomers, and said polymer adsorbs one optically active isomer preferentially;
   (d) shifting the temperature to a point where said polymer containing said adsorbed optically active isomer precipitates leaving the other optically active isomer substantially in solution;
   (e) separating said precipitate from the solution; and
   (f) isolating the optically active isomers independently from said precipitate and from solution by a process selected from the group consisting of filtration and partionining between water and an organic solvent;
   wherein said racemic amino acid is selected from the group consisting of tryptophan, phenylalnine and glutamic acid.

2. The process as described in claim 1, wherein said solvent is water.

3. The process as described in claim 1, wherein said solvent is an alcohol.

4. The process as described in claim 1, wherein said critical solution temperature is upper critical solution temperature.

5. The process as described in claim 1, wherein said critical solution temperature is lower critical solution temperature.

6. The process as described in claim 1, wherein said polymer is a homopolymer.

7. The process as described in claim 1, wherein said polymer is a copolymer.

8. The process as described in claim 1, wherein said comonomer is an N-alkyl or arylalkyl acrylamide, wherein said alkyl or arylalkyl moiety is a chiral moiety.

9. The process as described in claim 8, wherein said comonomer is chiral N-sec-butylacrylamide.

10. The process as described in claim 9, wherein said comonomer is S(+)-N-sec-butylacrylamide.

11. The process as described in claim 9, wherein said comonomer is R(−)-N-sec-butylacrylamide.

12. The process as described in claim 8, wherein said comonomer is chiral α-methylbenzylacrylamide.

13. The process as described in claim 1, wherein said amino acid is tryptophan.

14. A process of resolving a racemic amino acid into its optically active isomers, comprising:
   (a) preparing a solution of a chiral polymer in a suitable solvent, wherein said solvent is selected from the group consisting of water, alcohol, ether, amide, ester, ketone, and combinations thereof, further wherein said polymer is either a homopolymer of a chiral monomer, or a copolymer of N-isopropylacrylamide and a chiral comonomer, with said polymer exhibiting lower critical solution temperature behavior in said solvent;
   (b) maintaining said solution at a temperature less than said lower critical solution temperature such that the polymer stays in solution;
   (c) mixing the racemic amino acid intimately with said solution such that said chiral moieties shift said lower critical solution temperature differentially corresponding to the optically active isomers, and said polymer adsorbs one optically active isomer preferentially;
   (d) shifting the temperature to a point between the differential lower critical solution temperatures corresponding to the optically active isomers, such that said polymer containing said adsorbed optically active isomer precipitates leaving the other optically active isomer substantially in solution;
   (e) separating said precipitate from the solution; and
   (f) isolating the optically active isomers independently from said precipitate and from solution by a process selected from the group consisting of filtration and partionining between water and an organic solvent;
   wherein said racemic amino acid is selected from the group consisting of tryptophan, phenylalnine and glutamic acid.

15. A process of resolving a racemic amino acid into its optically active isomers, comprising:
   (a) preparing a solution of a chiral polymer in a suitable solvent, wherein said solvent is selected from the group consisting of water, alcohol, ether, amide, ester, ketone, and combinations thereof, further wherein said polymer is either a homopolymer of a chiral monomer, or a copolymer of N-isopropylacrylamide and a chiral comonomer, with said polymer exhibiting upper critical solution temperature behavior in said solvent;

(b) maintaining said solution at a temperature higher than said upper critical solution temperature such that the polymer stays in solution;

(c) mixing the racemic amino acid intimately with said solution such that said chiral moieties shift said upper critical solution temperature differentially corresponding to the optically active isomers, and said polymer adsorbs one optically active isomer preferentially;

(d) shifting the temperature to a point between the differential upper critical solution temperatures corresponding to the optically active isomers, such that said polymer containing said adsorbed optically active isomer precipitates leaving the other optically active isomer substantially in solution;

(e) separating said precipitate from the solution; and (f) isolating the optically active isomers independently from said precipitate and from solution by a process selected from the group consisting of filtration and partionining between water and an organic solvent;

wherein said racemic amino acid is selected from the group consisting of tryptophan, phenylalnine and glutamic acid.

16. The process as described in claim 14, wherein said racemic amino acid is tryptophan, said polymer is a copolymer of N-isopropylacrylamide and a chiral comonomer, said solvent is water and said isolation in step (f) is achieved by partitioning between water and an organic solvent.

17. The process as described in claim 16, wherein said comonomer is selected from the group consisting of chiral N-sec-butylacrylamide, chiral N-α-methyl benzylacrylamide, and combinations thereof.

18. The process as described in claim 17, wherein said comonomer is chiral N-sec-butylacrylamide.

19. The process as described in claim 18, wherein said comonomer is N-S(+)-sec-butylacrylamide.

20. The process as described in claim 18, wherein said comonomer is N-R(−)-sec-butylacrylamide.

21. A process of resolving racemic tryptophan into its optically active isomers, comprising:

(a) preparing a solution of a chiral polymer in water, wherein said polymer is either a homopolymer of a chiral monomer, or a copolymer of N-isopropylacrylamide and a chiral comonomer, with said polymer exhibiting lower critical solution temperature behavior in water;

(b) maintaining said solution at a temperature less than said lower critical solution temperature such that the polymer stays in solution;

(c) mixing racemic tryptophan intimately with said solution such that said chiral moieties shift said lower critical solution temperature differentially corresponding to the optically active isomers of tryptophan, and said polymer adsorbs one optically active isomer preferentially;

(d) shifting the temperature to a point between the differential lower critical solution temperatures corresponding to the optically active isomers, such that said polymer containing said adsorbed optically active isomer precipitates leaving the other optically active isomer substantially in solution;

(e) separating said precipitate from the solution; and (f) isolating the optically active isomers independently from said precipitate and from solution by a process selected from the group consisting of filtration and partionining between water and an organic solvent.

22. The process as described in claim 21, wherein said polymer is a copolymer of N-isoproprylacrylamide and a chiral monomer.

23. The process as described in claim 22, wherein said comonomer is selected from the group consisting of chiral N-sec-butylacrylamide, chiral α-methyl benzylacrylamide, and combinations thereof.

* * * * *